(12) United States Patent
Märin

(10) Patent No.: US 6,410,339 B1
(45) Date of Patent: *Jun. 25, 2002

(54) PREPARATION FOR DIAGNOSIS OF THE METABOLIC SYNDROME AND DISEASES INCLUDING THE SYNDROME

(75) Inventor: Per Märin, Göteberg (SE)

(73) Assignee: Cortenda AB, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,638
(22) PCT Filed: May 30, 1996
(86) PCT No.: PCT/SE96/00708
§ 371 (c)(1),
(2), (4) Date: Feb. 26, 1998
(87) PCT Pub. No.: WO96/38179
PCT Pub. Date: Dec. 5, 1996

(30) Foreign Application Priority Data

May 30, 1995 (SE) ................................. 9501991

(51) Int. Cl.$^7$ ............................ G01N 33/53; C12Q 3/00
(52) U.S. Cl. ..................... 436/500; 436/501; 436/516; 435/3; 435/4
(58) Field of Search ................................ 436/500, 501, 436/516; 435/4, 3

(56) References Cited

PUBLICATIONS

Atkinson, et al. : A weight–related intravenous dexamethosone . . . : Acta Indocrin.: 120, 6: pp. 753–759, 1989.*
Croughs, et al. : Comparison of oral and intravenous dexamethosome . . . : Acta Indocrin.: 72: pp. 51–62, 1973.*
Montwill, et al. : The overweight dexamethasone test is the procedure . . . : Steroids: 59: pp. 296–298, May 1994.*
Bennington, et al: Saunders dictionary & encyclopedia of laboratory medicing and technology: p. 398, Jan. 1987.*
Hormone and metabolic research, vol. 22, 1990 pp. 553–554 Hagg, et al; Salivory Control during an . . .
Neuropsychobiology, vol. 22, 1989: pp. 26–32 Maes et al; Results of the 8 a.m. dexamethasone . . .
DN Brindley, Role of glucocorticoids and fatty acids in the impairment of lipid metabolism observed in the metabolic syndrome, International Journal of Obesity (1995) 19, Suppl. 1 S69–S75.
Niklas Darin, Telko Amemiya, Bjorn Anderson, Sverker Jern and Per Bjorntorp, Cortisol Secretion in Relationship to Body Fat Distribution in Obese Premenopausal Women, Metabolism, vol. 41, No. 8 (Aug.) 1992 pp. 882–888.

(List continued on next page.)

Primary Examiner—Hankyel T. Park
Assistant Examiner—S. S. Brown
(74) Attorney, Agent, or Firm—Bradley N. Ruben

(57) ABSTRACT

The use of cortisol agonist for preparing a system for diagnosis of the Metabolic Syndrome and related conditions as belly fatness, insulin resistance including increased risk of developing senile diabetes, i.e., diabetes type II, high blood fats and high blood pressure, in which system the dose of cortisol agonist is in an interval where a difference is obtained in the inhibitory effect of the autoproduction of cortisol in individuals suffering from the Metabolic Syndrome, compared to normal values.

13 Claims, 1 Drawing Sheet

OTHER PUBLICATIONS

Rett–K, Wicklmayr–M, Standl–E, The metabolic syndrome, Pathopysiologic causes, diagnosis, therapy, Wien–Klin–Wochenschr, 1994; 106(24);750–7 published in Austria.

Gries–FA, Hubinger–A, Lipid metabolism and insulin resistance—clinical aspects and pathobiochemistry, Wein–Klin–Wochenschr 1994;106(24):763–7, published in Austria.

Steinmetz–A, Schafer–JR, Secondary disroders of lipid metabolism, metabolic syndrome and familial combined hyperlimidemia, Wein–Med–Wochenschr 1994; 144(12–13):299–307, published in Austria.

Muller–Wienand–D, Drone–W, Disorders of lipid metabolism in insulin resistance, Herz. Feb. 1995 20(1):33–46, published in Austria.

Moiseev–VS, Ivleva–AIA, Kobalava–ZHD, Hypertension, diabetes mellitus, atherosclerosis: clinical manifestations of metabolic syndrome X. Prospects of pharmacological treatment, Vestn–Ross–Akad–=Med–Nauk 1995(5):15–8, printed in Austria.

* cited by examiner

PREPARATION FOR DIAGNOSIS OF THE METABOLIC SYNDROME AND DISEASES INCLUDING THE SYNDROME

This application is the U.S. national stage filing under 35 U.S.C. 371 of application PCT/SE96/00708.

BACKGROUND

The metabolic syndrome is characterized by an increased amount of adipose tissue inside the abdominal cavity (popularly called belly fatness), insulin resistance with increased risk of developing senile diabetes, i.e. diabetes type II (=NIDDM, non-insulin dependent diabetes mellitus), high levels of blood fats and high blood pressure. Parallel to this is an increased risk of coronary, apoplexy, sudden death and other arteriosclerotic conditions.

A hypothetical explanation to the metabolic syndrome could be an overproduction of cortisol, a stress hormone which causes an accumulation of fat inside the abdominal cavity, and insulin resistance. Theoretically this could, through secondary metabolic effects, explain the other disorders related to the metabolic syndrome.

In Metabolism, vol. 41, No 8, 1992, pages 882–886, it is shown that belly fat women have higher secretion of cortisol than "evenly fat" women. The same work describes the effects of acute mental stress on the production of cortisol. It was shown that belly fat women, at a given stress signal, produced more cortisol than 'evenly fat' women. This suggested, but did not prove, that there may be a relationship between stress and belly obesity. A dexamethasone inhibitor test was carried out with 1 mg dexamethasone and subsequent measurement of cortisol content in serum. No difference in inhibitory effect on the production of cortisol could be found between the groups of belly fat women and evenly fat women and standard values.

Cortisol analogues, e.g. dexamethasone, have for many years been used to track so called endogenous (often hereditary) depressions in humans. The mechanism behind the test is however so far unknown.

OBJECT OF THE INVENTION AND MOST IMPORTANT CHARACTERISTICS

The object of the present invention is to find a diagnostic test by which individuals, running the risk of being affected by one or more of the symptoms and/or conditions characteristic to the above described metabolic syndrome, can be identified at an early stage. In the present invention this is accomplished by a diagnostic system, which as an active substance has cortisol agonists of a dose in an interval in which a difference in the inhibitory effect of the autonomous cortisol production between individuals with the metabolic syndrome or one or more of the related risk/conditions and normal values are obtained. Preferably the cortisol agonist is a synthetic cortisol analogues with a glucocorticoidal and/or mineral corticoidal effect, e.g. dexamethasone. The invention also concerns a diagnostic system for the purpose of diagnosing the metabolic syndrome, comprising a cortisol agonist of a dosage described above, and an agent for measuring the content of cortisol in saliva or serum.

DESCRIPTION OF THE INVENTION

The purpose of the invention is the novel medical use of cortisol agonists, which here refers to all synthetic cortisol agonists with glucocorticoidal and/or mineral corticoidal effects. The novel medical usage is as a diagnostic preparation for diagnosing the metabolic syndrome and related conditions such as belly fatness, insulin resistance, high blood fat and high blood pressure.

The invention emanates from the hypothesis that during chronic negative stress the hormone signal axis along cerebrum-hypothalamus-hypophysis-adrenal is strengthened, which secondarily likely leads to a down regulation of the GR (glucocorticoidal)—and/or MR (mineral corticoidal)—receptors (cf. Figure). This in turn could lead to a vicious circle where the inhibitory effect of GR and/or MR on CRF (cartocotropin releasing factor, a signal substance from hypothalamus stimulating the ACTH release from hypophysis)—secretion would attenuate. As a result of this the cortisol inhibition via the GR– and/or MR receptors would be weakened and thus, every given stress situation would lead to higher cortisol secretion (cf. Figure).

In an attempt to test the above hypothesis we have in a scientific study measured the basal concentration of cortisol and then given dexamethasone, a synthetic cortisol analogue, that is a synthetic hormone substance with the effect of cortisol, at varying dosage. The idea was that patients having the GR and/or MR receptors down regulated should have their cortisol production less inhibited when using dexamethasbne (an example of a synthetic cortisol analogue) at low doses, particularly when compared to the initial value, which often may be somewhat higher in healthy persons. The inferior inhibitory effect is thus related to the uninhibited cortisol production. When tested on persons having normal weight, general overweight and on belly fat persons, we found that the hypothesis agrees with reality. Belly fatness is fatness inside the abdominal cavity in contrast to general fatness. Those belly fat individuals had also significantly lower basal cortisol values at 8.00 o'clock when comparing serum cortisol with the control. Values over or equal to 400 nmol/l were here considered normal values.

The trial group was 22 men between 40 and 60 years. Eight of them were not fat according to the BMI (body mass index) definition $<25$ kg/m$^2$ and 14 were fat with a BMI>25. 12 men had a WHR (waist hip ratio) <1.0 and 10 had a WHR>1.0.

Dexamethasone was administered in doses of 0.05, 0.125, 0.25 and 0.5 in an arbitrary order with 1 week intervals.

Dexamethasone was taken at 22.00 o'clock and the cortisol content was measured at 8.00 o'clock on the following morning. To establish the inhibitory effect at least 3 hours and at most 24 hours should pass between the intake of the cortisol agonist and measurement of the cortisol content.

Figure 1:
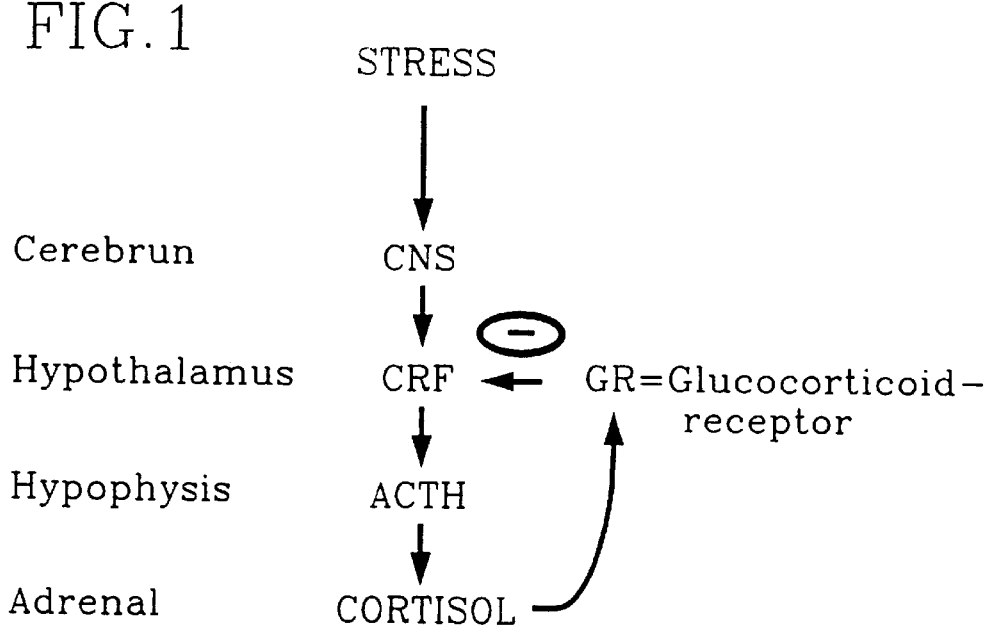
FIG. 1 shows the hormone signal axis along the cerebrum-hypothalamus-hypophysis-adrenal.
Figure 2:
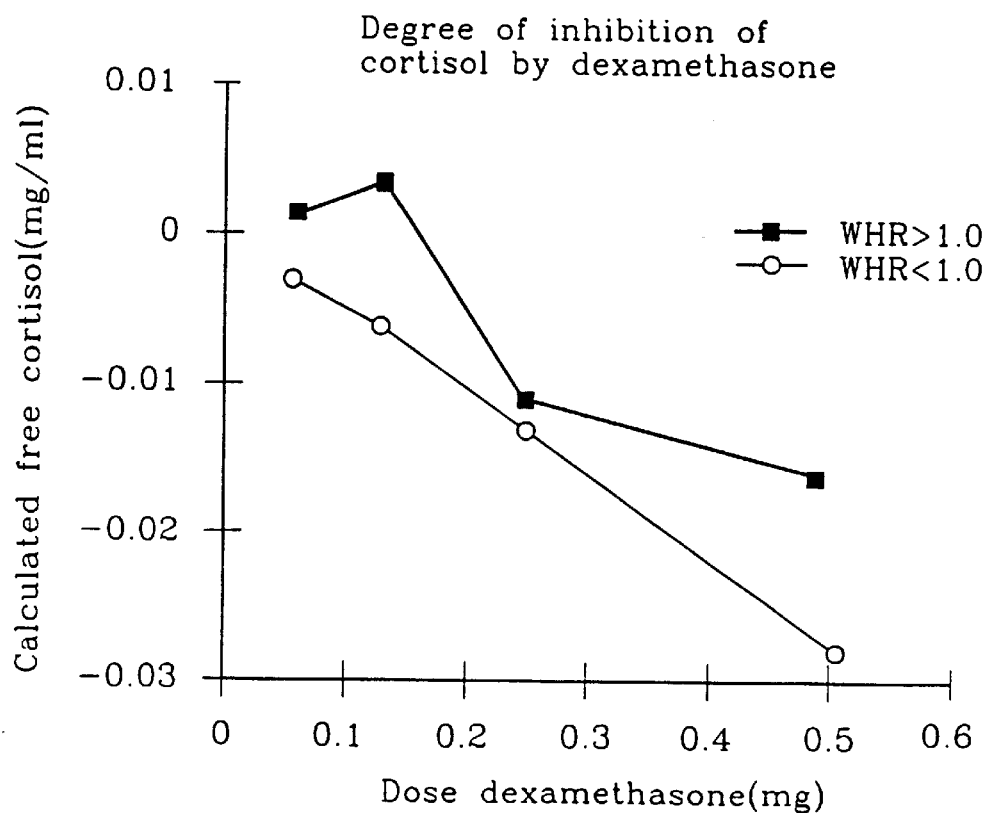
FIG. 2 shows serum cortisol readings after different doses of dexamethasone given to two groups of individuals, divided according to their body fat distribution.

FIG. 2 shows differences (delta values) between measured cortisol content and basal values (not inhibited) after different doses of dexamethasone. A comparison has been made between men with WHR<1.0 (open squares) and men with WHR>1.0 (filled squares).

Belly fat individuals were thus shown to have significantly inferior inhibition by dexamethasone (a synthetic cortisol analogue) at low doses. The effect was found at doses between 0.05 and 0.5 mg. This should be compared to the above-mentioned test in which no effect could be established at a dose of 1 mg dexamethasone. Thus it has now surprisingly been shown that with low doses of dexamethasone a significantly inferior inhibition of the autoproduction of cortisol by belly fat individuals is obtained.

For normal weight individuals with and those with general overweight but without belly fatness inhibition of the autoproduction of cortisol was obtained already at a dose of 0.05 mg and continuously up to maximum inhibition at 1 mg (for a few also at 0.5 mg).

For 'dangerously' belly fat individuals we found that the inhibition could not be measured until the dose was increased to 0.25 mg. Thereafter the maximum inhibitory dose was the same as for healthy individuals, i.e. maximum inhibition in the interval 0.5–1 mg.

This means that for belly fat individuals the inhibition curve is shifted towards the right. Critical doses which we found significant differences in the material (about 20 individuals) are 0.125 mg and particularly 0.5 mg (most distinct difference with this dose).

For the first time it is also shown that there is a, so-called dose-response curve, for the dexamethasone test, by which differences can be detected between individuals at risk of developing the metabolic syndrome and/or individuals with one or several risk factors/conditions related to the metabolic syndrome, when compared to healthy individuals.

The above mentioned doses hold for the tested substance dexamethasone. The effective dose varies for different cortisol agonists. Crude conversions of effective doses of the different cortisol agonists are found in the literature e.g. in FASS.

The cortisol agonist, that in this investigation was dexamethasone, was administered as a tablet. The cortisol content was measured twice in serum.

In the same investigation the cortisol content was in parallel measured in saliva for a small number of individuals. This was done with a standardized quid (Salivette), which the patient keeps in his mouth for about 45 seconds and thereafter seals in a simple and standardized way. The quids were then analysed for cortisol content. In the test we then found a good correlation between the cortisol content in serum and in saliva.

The invention also concerns a diagnostic system comprising a cortisol agonist as described above, and means to measure the cortisol content in saliva or in serum with the aim of measuring the inhibitory effect on the cortisol production. Such means for measuring the cortisol content are available as standard devices. The diagnostic system may also involve means to measure the basal cortisol content since, as shown above, it has been established that belly fat individuals have significantly lower basal cortisol values (less than 400 nmol/l serum) compared to normal population. By measuring at least at two different doses of the cortisol agonist (in the case of dexamethasone at 0.125 and 0.5 mg), and constructing an inhibitor curve taking into account both the measured inhibitory effect and the measured basal cortisol concentration, a very specific diagnostic test is obtained.

What is claimed is:

1. A method for diagnosing Metabolic Syndrome in an individual, said method comprising:
    (a) administering a cortisol agonist to said individual;
    (b) determining the inhibitory effect of said cortisol agonist on the production of cortisol by said individual between 3 and 24 hours after administering said cortisol agonist; and
    (c) diagnosing said individual for Metabolic Syndrome based on the inhibitor effect determined.

2. The method of claim 1, wherein step (b) comprises measuring the cortisol content in said individual.

3. The method of claim 2, wherein the cortisol content in serum or in saliva is measured.

4. The method of claim 1, further comprising measuring the basal cortisol content prior to administration of the cortisol agonist.

5. A method of diagnosing an individual for being at risk of being affected by Metabolic Syndrome, said method comprising:
    (a) administering a cortisol agonist to said individual;
    (b) determining the inhibitory effect of said cortisol agonist on the production of cortisol by said individual between 3 and 24 hours after administering said cortisol agonist; and
    (c) diagnosing said individual for being at risk of being affected by Metabolic Syndrome based on the inhibitory effect determined.

6. The method of claim 1, wherein said cortisol agonist is a synthetic cortisol analogue which has (i) a glucocorticoid effect or (ii) a mineral corticoid effect or (iii) both a glucocorticoid and a mineral corticoid effect.

7. The method of claim 6, wherein the cortisol agonist is dexamethasone.

8. The method of claim 7, wherein the dose of dexamethasone is between about 0.05 and about 0.5 mg.

9. The method of claim 8, wherein the dose of dexamethasone is between about 0.125 and about 0.5 mg.

10. The method of claim 1, wherein at least two different doses of said cortisol agonist are administered at intervals.

11. The method of claim 10, wherein said cortisol agonist is dexamethasone and said at least two different doses are 0.125 mg. and 0.5 mg.

12. A diagnostic kit comprising: (a) a dosage of a cortisol agonist present in an amount effective for determining a difference in the inhibitory effect of the autoproduction of cortisol in an individual having or at risk of having Metabolic Syndrome or one of its risk factors when compared with a person not so affected from 3 to 24 hours after administration of said agonist; and (b) means for measuring cortisol content in a clinical sample from 3 to 24 hours after administration of said agonist.

13. A method for diagnosing an individual for being at risk of being affected by at least one of the symptoms of the Metabolic Syndrome, said method comprising:
    (a) administering a cortisol agonist to said individual;
    (b) determining the inhibitory effect of said cortisol agonist on the production of cortisol by said individual between 3 and 24 hours after administering said cortisol agonist; and
    (c) diagnosing said individual for Metabolic Syndrome based on the inhibitor effect determined.

* * * * *